United States Patent [19]

Servos et al.

[11] 3,942,515

[45] Mar. 9, 1976

[54] AIR CALORIC STIMULATION SYSTEM

[75] Inventors: Gerald H. Servos, Glen Ellyn; Kenneth R. Horning, River Forest, both of Ill.

[73] Assignee: Instrumentation & Control Systems, Inc., Addison, Ill.

[22] Filed: Sept. 11, 1974

[21] Appl. No.: 504,864

[52] U.S. Cl. .............. 128/2 R; 128/2 N; 128/2.1 M; 237/2 R
[51] Int. Cl.² ..................... A61B 19/00; A61B 5/05
[58] Field of Search ............ 128/2.1 M, 2.1 R, 2 N, 128/2 S, 2 T, 2 R; 237/2; 236/1 F, 3, 10

[56] References Cited
UNITED STATES PATENTS

| | | | |
|---|---|---|---|
| 2,192,276 | 3/1940 | Schaefer | 236/3 |
| 2,495,861 | 1/1950 | Newton | 236/10 X |
| 2,823,863 | 2/1958 | Moyes | 237/2 R |
| 3,000,271 | 9/1961 | Harvey et al. | 128/2.1 M |
| 3,155,157 | 11/1964 | Anderson et al. | 236/1 F X |
| 3,563,231 | 2/1971 | Ducote et al. | 128/2.1 M |
| 3,794,017 | 2/1974 | Servos | 128/2.1 M |

*Primary Examiner*—Kyle L. Howell
*Attorney, Agent, or Firm*—Alter and Weiss

[57] ABSTRACT

The air caloric stimulation system provides an adjustable air system with accurate and automatic control of the delivery and temperature of air. A thermal electric device utilizing the Peltier effect generates or absorbs heat depending on the difference between the temperature of the air at the outlet and the "set" or desired temperature of the air at the outlet. Further, the Peltier units are aided in controlling the temperature of the air using a radiator system in conjunction with a liquid circulating system. The current to the Peltier units are controlled using unique proportional phase controlled signals. Safety circuitry prevents the air or liquid from overheating.

16 Claims, 6 Drawing Figures

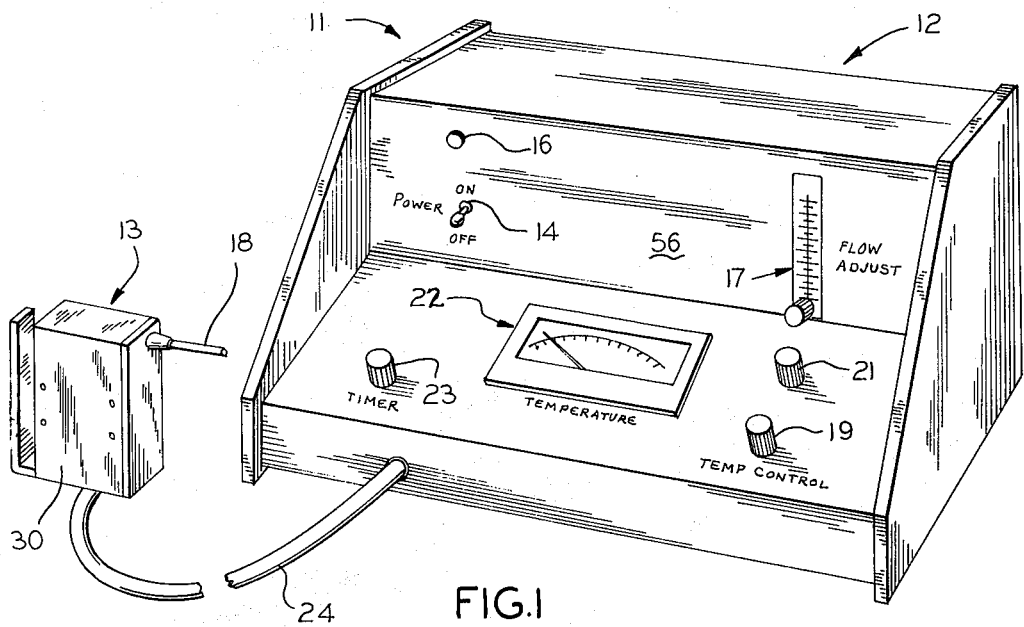
FIG.1
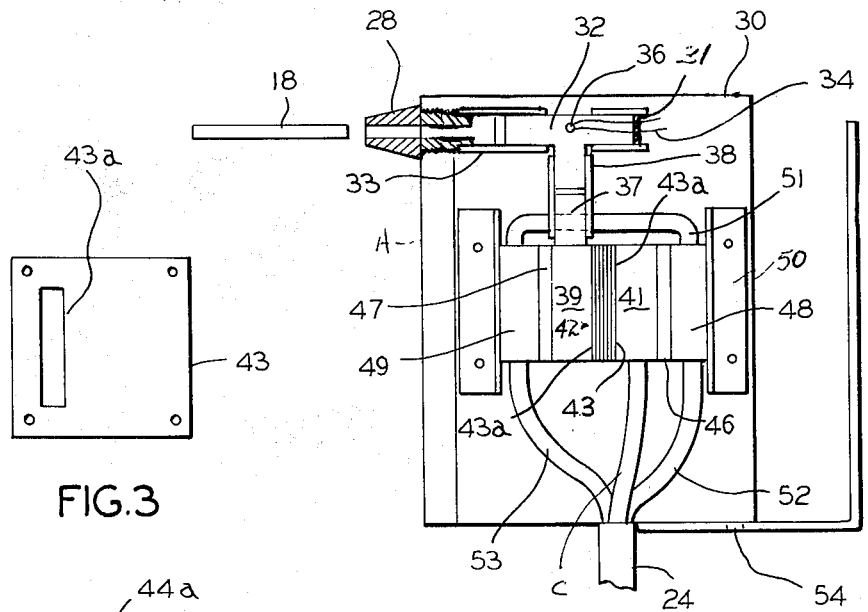
FIG.2
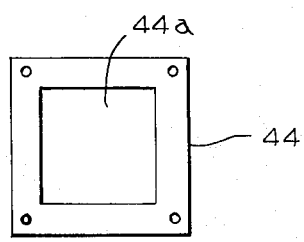
FIG.3
FIG.4

AIR CALORIC STIMULATION SYSTEM

This invention relates to systems used for measuring vestibular responses in the human body and more particularly, to systems for controlling the flow and temperature of air used in eliciting a nystagmus response.

Caloric testing has grown to be an indispensible and integral part of the clinical evaluation of patient's equilibratory and vertiginous disorders. Such testing enables the ontoneurologist to assess the functional status of each ear separately by measuring the reflex responses generated by thermal stimulation of the non-auditory labyrinth of the ear. For a long time water caloric tests were employed to determine nystagmus responses. Subsequently, temperature controlled water was used to elicit the nystagmus responses.

The equipment described herein is practical utilization of thermally controlled air as a stimulating means. When using water for eliciting the nystagmus responses, the water necessarily overflows the ears and is uncomfortable to the patient, messy to handle and requires continuous maintenance and cleaning.

An object of the present invention is to provide a new and unique air caloric stimulation system.

A related object of the present invention is to provide such systems using liquid as the thermal transmission media between the heating and cooling elements and the actual air used.

Yet another object of the present invention is to heat or cool the air using thermal electric devices based on the Peltier effect which generates or absorbs heat as a function of current flow through semi-conductor elements. The elements are stacked together to form a semi-conductor pile thereby multiplying their effectiveness. Current in one direction cools the inside elements and current in the reverse direction warms the inside elements. Liquid bearing radiators are used as thermal transmission elements to aid in controlling the temperature of the piles. The air is forced through the ducts to be either warmed or cooled by the piles.

Yet another object of the invention is to provide controls for controlling the actual time duration of the air calorization, and the delivered temperature as well as the rate of flow of the air.

Nystagmus may be induced by many known methods. Under conditions of nystagmus the eyeball oscillates moving to the right or left side of the eye cavity in the cranium. When the eyeball reaches the limit of such movement, it moves back towards the starting position at a relatively higher rate of speed than it moved when going away from the starting position.

Nystagmus is induced by varying temperature of the semicircular canals. This is done by heating or cooling the tympanic membrane above or below body temperature.

It is thus a feature of this invention to provide for practically utilizing air for varying the caloric conditions of the left or right semi-circular canals, thereby inducing nystagmus.

The above mentioned and other objects and features of this invention will become more apparent from a description of the apparatus from the following specification taken in conjunction with the accompanying drawings, wherein:

FIG. 1 is a pictorial representation of the air caloric stimulation system apparatus;

FIG. 2 is a showing of the head of the system shown attached in FIG. 1 and showing details of the thermal electric device or thermal transmission i.e. thermal electric pile;

FIG. 3 and FIG. 4 are details of the plates of the air heat exchanger;

Figure 5:
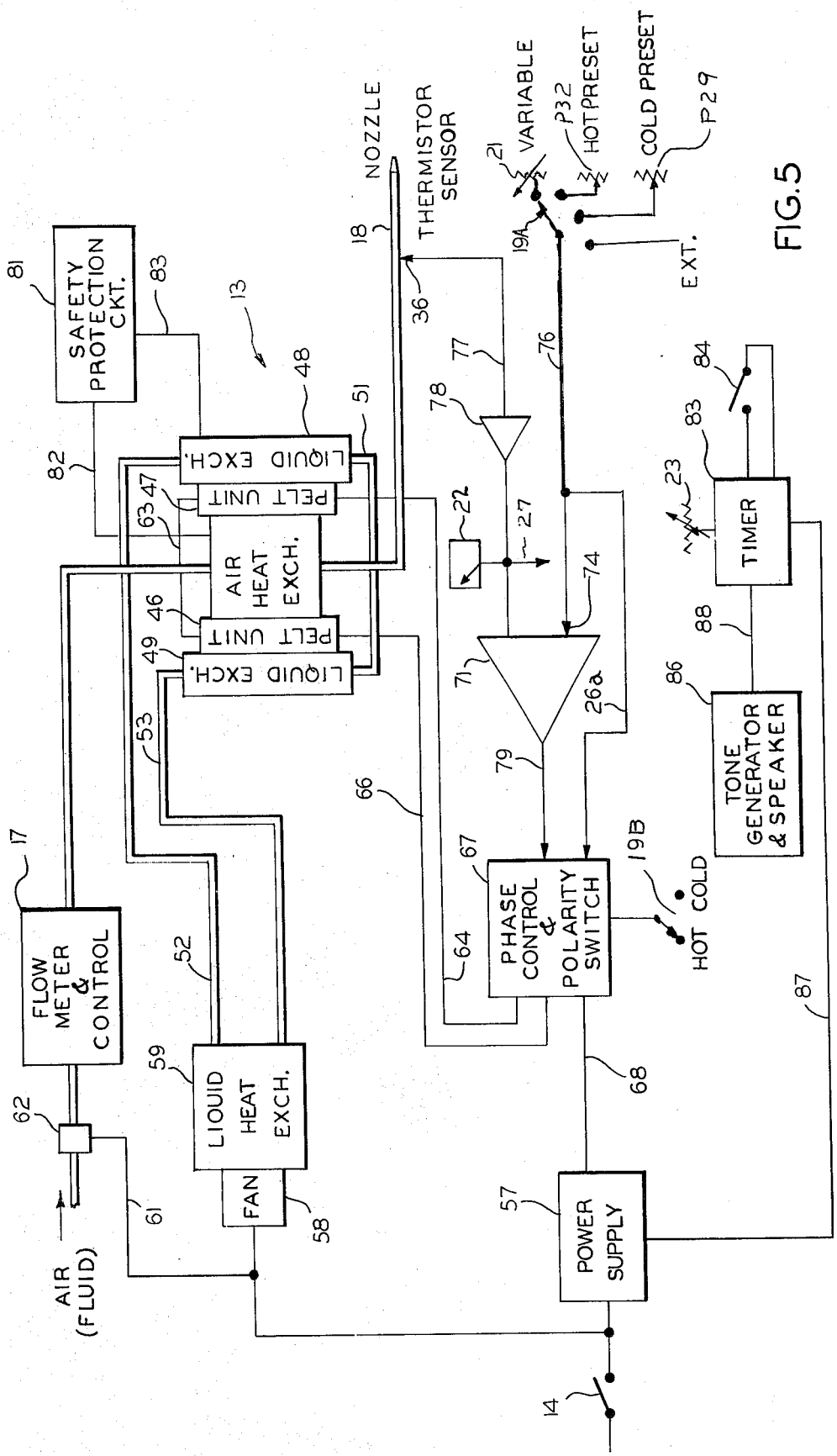
FIG. 5 is a block diagram of the air caloric system shown herein.

In the pictorial drawing of FIG. 1 the overall air caloric system apparatus is shown as 11. It comprises basically the power supply and control unit 12, along with the thermal electric delivery head 13.

The control unit 12 includes a power "on-off" switch 14, a pilot light 16 indicating when power is on, a flow adjust control 17, which adjusts the flow of the air coming out of the delivery head 13 at the replaceable nozzle 18. Temperature control knobs 19 and 21, along with a temperature meter 22, are further shown on the control unit 12. A timer control knob 23 controls the lapsed time before a signal indicates that the nozzle 18 of the delivery head 13 should be removed from the patient's ear.

The electrical, liquid, and air connections between the head 13 and the control unit 12 are provided through a basic umbilical cord 24. As shown in the sectional view of FIG. 2, the case 30 encloses the thermal electric unit and the heat exchange unit used for either adding or removing heat to bring the air to the temperature required and maintaining it at that temperature.

The head is movable so that the air can be easily applied to the patient's ears as required. The air is applied through the nozzle 18 which is replaceable. A plastic or rubber nipple 28 is applied to a plate A at one corner thereof to attach to the air system coming from the air exchanger. The nipple is attached to a plate A mounted to the outside of the case. The nipple 28 is further attached to a plastic or non-heat conducting material T-coupling 32 with a rubber or plastic section 33. The other opening of the T-coupling is blocked, as indicated at 31, to the flow of air, but means are provided for receiving electrical conductors, such as electrical conductor 34 for attachment to thermistor 36 which monitors the temperature of the outgoing air.

The vertical portion of the T-coupling 32 is coupled to an output tube or barbed fitting 37 of the air exchanger unit with a rubber or plastic section 38. The output tube 37 is connected directly to an outgoing connecting plate 39. The outgoing connecting plate 39 is connected to the incoming connecting plate 41 through air duct system 42. Air flow enters the incoming connector plate through tube C of the umbilical 24.

The air duct system 42 is made up of a series of plates, such as plate 43 and plate 44, shown in FIG. 3, and FIG. 4, respectively. These plates are placed alternately for example, the first plate on the right hand side of the air duct unit 42 would be a plate similar to plate 44 so that the air would have to travel the entire height of connecting plate 41.

Similarly, the last plate in the duct work 42 is also a plate, like plate 44. This causes the air to travel the maximum distance in getting to the outlet pipe 37. The remaining plates are alternately 43 and 44. A total of three plates 44 and two plates 43 are used between connecting plates 39 and 41. Here, again, the air is forced to travel over a large distance and has time to stabilize at the temperature of the thermal electronic Peltier units 46 and 47. The Peltier units used are the Borg Warner model 940 TE modules. A water heat exchanger is also provided at the Peltier units, and are shown as liquid heat exchangers 48 and 49 joined together by coupling pipe 51. The water comes from umbilical cord which includes water tube 52 and enters heat exchanger 48. From heat exchanger 48 the liquid passes through tube 51, heat exchanger 49, through tube 53 and back to the umbilical cord 24. The unit comprising the connecting plates, the heat exchangers and the Peltier units are held in place using flanges, such as flange 50, for example.

The block diagram of FIG. 5 shows how the controls located in cabinet 12 with the head 13. An "on-off" switch 14 shown on the front panel 56 is provided to activate the unit. Basically it connects 120 V 60 cycle power. Of course, it could easily also connect other types of power sources, such as 220 V 50 cycle power when used in markets utilizing such power.

The basic power is converted by a power supply 57 to regulated and unregulated direct current power. The alternating current power is also connected to operate a fan 58 which works in conjunction with a remote liquid heat exchanger 59. The heat exchanger 59 is basically a coil going through a radiator and a fan is attached thereto to dissipate the heat brought back from the Peltier thermal element unit of the head 13.

Thus, the liquid heat exchanger system has a pump in it (not shown) at 59 which forces the heat exchanger liquid through tube 52 into the liquid heat exchanger unit 48, coupling tube 51 to the liquid exchange unit 49 and out through tube 53 back to the remote liquid heat exchanger 59 located in the cabinet.

The alternating current coming through switch 14 is also coupled through conductor 61 to an optional internal air pump 62 which generates air flow through the air heat exchanger into the ear. The amount of air flowing is adjusted using the flow meter and control shown as 17 on the panel 56 of the control unit 12. It adjusts the amount of air flowing through the air heat exchanger which is designed to maintain a stable set temperature of this air.

The Peltier units 46 and 47 are shown serially interconnected through conductor 63 and connected to a phase control and polarity switch 19B through conductors 64 and 66, respectively. The phase control and polarity switch is energized by the power supply over conductor 68. It is capable of setting the air coming from the system either for hot or cold temperatures depending on the position of switch 19B. The switch 19B, as will be seen in conjunction with FIG. 6, aids in setting the phase of the current going to the Peltier unit so that the Peltier units are either operating to generate heat or to dissipate heat.

Thus, while not actually seen in the block diagram switch 19B controls the connection of conductors 64 and 66 into phase control and polarity switch 67. This will be seen in greater detail in the description of the schematic of FIG. 6.

Figure 6:
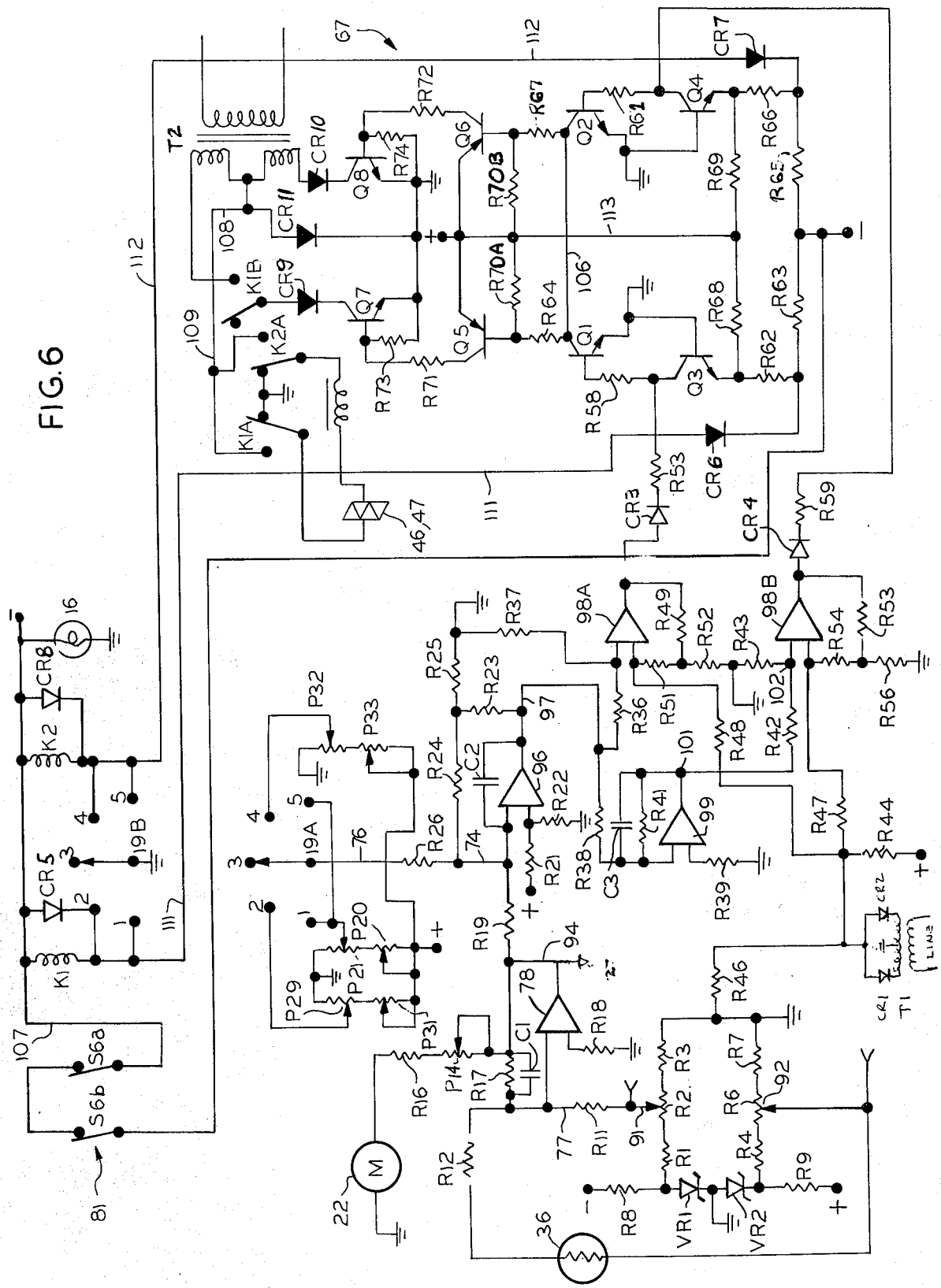
FIG. 6 is a schematic drawing of the pertinent portions of the air caloric system controls.

The temperature of the air coming from the head 13 is set through the use of switch 19A which connects one input of control amplifier 71 to either a variable signal level source or a preset signal level source. The variable signal level source, of course, corresponds to a temperature range while the preset control corresponds to a given temperature. The temperature range is obtained by manipulating control potentiometer P21 on the front panel of unit 12. The switch 19 also can connect to an external voltage source for external temperature control, when that is desired. The cold preset and warm preset potentiometers P29 and P32, respectively are shown in FIG. 6. Thus, the signal level received from either the potentiometer P21, the cold preset potentiometer P29 or the warm preset potentiometer P32 or the external control is fed into one end of the control amplifier. The difference between the set signal level received at the input 74 of amplifier 71 over conductor 76 and the signal level indicating the actual temperature of the air originating at thermistor 36 in the nozzle received and extending through conductor 77 and amplifier 78 is the actual temperature signal input to the control amplifier. The actual temperature output of preamplifier is monitored on the meter 22 or on a recorder which may be connected to the output of preamplifier 78 at arrow 27.

Means are provided for assuring that the temperature in the head does not rise to the point where it damages the Peltier units. Such safety means are indicated in the block diagram by the safety protection circuit block 81 shown coupled to the air heat exchanger and the liquid heat exchanger of head 13 by arrows 82 and 83, respectively. Thus, for example, if the nozzle 18 is blocked and the air heats up to a critical temperature, then the safety protection circuit 81 automatically opens the energization circuit to the Peltier units to prevent current from going through the Peltier units thus removing the source of heat. Similarly, if the liquid heat exchanger gets too hot, indicating a malfunction in the operation of the unit, then the current to the Peltier units is also stopped.

Means are provided to automatically notify the operator who is using the system that he has been injecting air into the ear for the prerequisit time. The time is set by the timer control 23 which is shown in the block diagram as an adjustable potentiometer connected to an electronic timer shown as 83. When the operator of the unit injects the nozzle into the patient's ear, he operates the switch 84 which conveniently may be a foot switch. This initiates the timer operation. At the end of the time desired a tone generator and a speaker unit 86 connected to the timer by conductor 88 operate to sound an alarm tone. The operator at the tone signal removes the nozzle from the ear of the patient.

The timer is powered by power supply over conductor 87. Thus, ideally a control valve or alternatively an air pump 62 is operated to start the air flowing through the flow meter and control. The flow meter and control is set so that a desired amount of air flow is obtained. The air goes through the air heat exchanger which is automatically brought to the required temperature by various means, such as Peltier units. Thus, the current either flows into the Peltier unit 46 and out of the Peltier unit 47 or vice versa, depending on whether the thermal element is heating or cooling as dictated by switch 19.

The amount of current and the polarity of the current is controlled automatically by the control amplifier 71 which receives a pair of signals, one signal is received from the thermistor sensor 36 located at the nozzle 18 and the other signal is received from the controls used for setting the desired air temperature. When these temperatures are different than the control amplifier in conjunction with the phase control and polarity switch, circuitry 67 causes a current to flow through the Peltier units either to generate heat or to dissipate heat.

The preferred circuitry of the pertinent portions of control amplifier 71 along with the preamplifier 78 and the phase control and polarity switch 67 are shown in greater detail in FIG. 6.

Means are provided for converting the actual temperature of the air going into the patient's ear into a calibrated signal. More particularly, a sensor, such as the thermistor sensor 36 is shown coupled to a bridge circuit comprising resistor R1, variable resistor R2 and resistor R3 series connected in one leg. The other leg comprises resistor R4, variable resistor R6 and resistor R7. The junction point of resistor R3 and resistor R7 is grounded.

Resistors R1 and R4 are connected to reference voltages provided by zeners VR1 and VR2. Bias current is provided by resistor R8 from a negative regulated power supply for zener VR1. Likewise, bias current for zener VR2 is supplied through resistor R9 from a positive regulated power supply.

The thermistor sensor 36 is coupled between the wipers 92 of the variable resistor R6 and resistor R12. (Resistor R12 acts to linearize the output of the thermistor sensor 36.) This series connection forms one leg of the bridge circuit. Resistor R11 is connected to wiper of resistor R2, which forms another leg of the bridge. Coupled to the common connection of resistor R11 and R12 is the negative input of linear operational amplifier 78.

Means are provided for monitoring the temperatures of the air used in the nystagmus operation. More particularly, the output of amplifier 78 is connected through conductor 94, variable resistor P14, resistor R16 and through the meter 22 to ground. The meter is calibrated using variable resistor P14 to provide a direct temperature reading. The output 94 of amplifier 78 becomes more negative with higher temperatures. The resistors R16 and P14 assure that the meter reading reflects the temperature. A terminal, indicated by arrow 27, is provided for connecting an external recorder at this point if desired. The feedback circuit of amplifier 78 extends from the output conductor 94 through resistor R17 bridged by capacitor C1. The positive input of amplifier 78 is connected to ground through resistor R18.

Means are provided for comparing the "set" temperature and the actual temperature of the air used in the nystagmus. More particularly, the output of amplifier 78 is connected to the negative input of amplifier 96, through resistor R19. The operational amplifier 96 is connected as a linear amplifier — more particularly as a servo, or error, amplifier. It amplifies the difference in current flowing through resistors R19 and R26. The current through resistor R19 is proportional to the actual temperature being monitored. The current through resistor R26 is proportional to the desired temperature. When these two currents are equal in absolute value, the net current input into the servo amplifier is negligible, and the output 97 is near zero volts at this stable operating condition. The feedback circuit for amplifier 96 comprises resistors R23, R24 and R25 connected between output 97 and the negative input of the amplifier. The junction of resistors R23 and R24 is coupled to ground through resistor R25. The series connection of resistors R23 and R24 is bridged by capacitor C2. Resistors R21 and R22 are used to bias amplifier 96 such that when the current through resistor R26 is zero (input 76 at ground) some current is required through resistor R19 for a stable operating temperature. This bias is required to prevent the actual temperature from ever reaching 0° C which could cause freezing of any moisture present in the air supply. Furthermore, the adjustments of potentiometers P29 and P32 are set to provide two fixed temperatures for operator convenience (i.e. no manual adjustments required). This is set at the time of manufacture, but can be readjusted as desired.

Switch 19 is assembled so that in position 1, the wiper of level 19A is connected to positive regulated voltage through adjustable resistors or potentiometers P20, P21, P29, P31, P33 and P32. In a preferred embodiment of this invention the adjustment of potentiometers P20, P31 and P33 is set at the time of manufacture to provide a maximum obtainable temperature of 50° C when the wipers of potentiometers P21, P29 and P32 are at their maximum (away from ground) positions. However, the adjustment of potentiometer P21 is varied by the adjustment of knob 21 on the front panel of the instrument to enable varying the temperature setting.

When switch 19 is in position 1, the operation of knob 21 varies the cool adjustment. When switch 19 is in position 2, the wiper of level A is connected to positive regulated voltage through potentiometers P29 and P31. When the wiper is in position 3, there is no signal input from switch 19. When the wiper is in position 4, it is connected to positive regulated voltage through potentiometers P32 and P34.

When the wiper of level A of switch 19 is in position 5, it is connected to positive regulated voltage through potentiometers P21 and P22 and the warm temperatures can be adjusted by operating temperature control knob 21. The signal output of the preamplifier 78 which represents the actual temperature is thus added to the set signal received from switch 19. The difference is the "error" signal which is the input signal to the amplifier 96.

Means are provided for synchronizing the output signal of amplifier 96 to line frequency to provide a signal having a period equal to twice the line frequency period and a signal whose width or time duration is a function of the "error" amplitude. Actually, two signals 180° out of phase are provided, one for warm temperature control and one for cold temperature control. More particularly operational amplifiers 98A and 98B which are connected as comparators are provided. The output of amplifier 96 is connected to the negative input of cool temperature control comparator 98A through a voltage divider comprising resistors R36 and R37 series connected to ground. The junction of resistors R36 and R37 is connected to the negative input of comparator 98A. The output of amplifier 96 is also connected to a warm temperature control comparator 98B, but this connection is made through a unity gain inverter amplifier 99. Thus, the output of amplifier 96 is connected to the negative input of inverter amplifier 99 through resistor R38.

The positive input of amplifier 99 is coupled to ground through resistor R39. Feedback is obtained by connecting the output 101 of amplifier 99 through resistor R41 bridged by capacitor C3 connected to the negative input of synchronizing comparator 98B using a voltage divider network comprising resistors R42 and R43 connected in series to ground. The junction point 102 of resistors R42 and R43 is coupled to the negative input of synchronizing comparator 98B.

Negative fullwave rectified line frequency voltage is provided for synchronizing comparators 98A and 98B by the connection of transformer T1. The rectifiers CR1 and CR2 are connected to form a full wave center tapped rectifier circuit providing a signal of twice line frequency across resistor R46. Resistor R44 provides some current sinking near the zero crossover point. This minimizes undesired filtering due to stray capacitances. The junction of resistors R44 and R46 is connected to the positive input of comparator 98B through resistor R47 and to the positive input of comparator 98A through resistor R48.

The positive feedback circuit for comparator 98A goes from the output of amplifier 98A through resistor R49 in series with resistor R51 to the positive input of amplifier 98A. The junction of resistors R49 and R51 is coupled to ground through resistor R52. Similarly, the positive feedback of amplifier 98B goes from the output of amplifier 98B through resistor R53 connected in series with resistor R54 to the positive input of amplifier 98B. The junction of resistors R53 and R54 is connected to ground through resistor R56.

The outputs of comparators 98A and 98B are synchronized to the line frequency so that they both provide signals having periods equal to twice the line signal periods. The form of the output signal from the synchronizing amplifiers 98A and 98B are square waves. The time duration of the positive portion of the square waves are a function of the amplitude of the "error" signal and only the positive portions of the signal are used.

Either the output of amplifiers 98A or 98B are used for the phase control and polarity switch circuit 67. When the actual temperature is warmer than the set temperature, then the "error" signal at 97 is positive and the output of comparator 98A is a negative signal level and the output of comparator 98B is a square wave whose positive portions are a function of the error amplitude. When the actual temperature is cooler than the set temperature, then a positive square wave signal is obtained at the output of comparator 98A and the signal at the output of comparator 98B is a negative signal level. The negative signal levels are not used. The output of amplifier 98A is connected to the base of transistor Q1 through diode CR3, connected to pass the positive signals, and resistors R57 and R58 in series. In a similar manner the output of comparator 98B is connected to the base of transistor Q2 through diode CR4, connected to pass the positive signals, and resistors R59 and R61 in series.

The determination of which transistor Q1 or Q2 controls the operation of the circuit 67 is made by the operation of the rotary switch 19. If the rotary switch is in the cooling mode, i.e. positions 1 or 2, then the output of the comparator 98A is controlling through transistor Q1. If the rotary switch is in the heating mode, i.e. positions 4 or 5, then the output of the amplifier 98B controls through transistor Q2.

With switch 19 operated to positions 1 or 2, ground is placed on one end of relay coil K1. The other end of relay coil K1 is connected to negative voltage over a circuit that extends through conductor 107, and temperature sensitive switches S6a and S6b. These switches are actually in contact with the liquid and air heat exchangers and comprise safety circuit 81. The coil of relay K1 is bridged by diode CR5 for spark suppression.

The energization of coil K1 actuates contacts K1A and K1B. The operation of the contact K1 connects negative voltage from the floating ground midpoint 108 of the secondary coil of transformer T2 through conductor 109, operated contacts K1A and the Peltier thermal electric elements 46, 47 and unoperated contacts K2A to ground. Actually elements 46, 47 comprise two elements in series, but for simplification, it is here (in FIG. 6) shown as one element.

The time length or phase of the output signal, i.e., the signal going through elements 46, 47 is controlled by the phase control circuitry as a function of the output of either comparator 98A or comparator 98B. With switch 19 in positions 1 or 2 (the cooling mode) ground is placed on the emitter of transistor Q3 over a circuit that extends through the wiper of level B of switch 19 in positions 1 or 2, conductor 111, diode CR6 and resistor R62. Resistor R62 is tied to negative voltage through resistor R63. When the ground signal from switch 19 is placed at the junction of resistors R62 and R63, the transistor Q3 is "off" or non-conducting and allows the signal originating at the output of comparator 98A to be coupled through diode CR3, resistors R57 and R58 into the base of transistor Q1.

When switch 19 is in positions 4 or 5 (the heating mode) transistor Q3, an NPN transistor, is in its normally conducting mode. When transistor Q3 conducts, it shunts the signal at the junction of resistors R57 and R58 therethrough, since the base of transistor Q3 is tied to ground and its emitter is tied to the negative voltage through resistors R62 and R63 in series and to positive battery by resistor R68.

The emitters of NPN transistors Q1, Q2 are tied directly to ground. The collectors of transistors Q1, Q2 are tied together through conductor 106 and to the bases of transistors Q5, Q6 through resistors R64 and R68, respectively. The bases of transistors Q5, Q6 are tied to positive voltage through resistors R70A, R70B, respectively. When transistor Q3 is turned off, transistor Q1 is enabled and switches responsive to the positive signal from amplifier 98A.

When either transistor Q1 or Q2 conducts, then both PNP transistors Q5 and Q6 conduct. The collectors of transistors Q5 and Q6 are connected to power transistors Q7, Q8. Actually, every thing between comparator 98 and the power transistors Q7, Q8 should be considered the phase control circuit. Thus, the collectors of transistors Q5 and Q6 are connected to the base of transistors Q7, Q8 through resistors R71 and R72, respectively. The bases are also connected to ground through resistors R73 and R74, respectively. The emitters of both transistors are connected directly to ground. The collector of transistor Q7 is connected to the top side of the secondary of transformer T2 through the K1B contact when it is actuated and through diode CR9. The collector of transistor Q8 is connected to the bottom side of the secondary of transformer T2 through diode CR10. The midpoint of the secondary of the transformer T2 is connected to ground through the diode CR10.

While there is a positive going signal at the output of comparator 98A, transistor Q1 conducts and causes transistors Q5, Q6 to conduct. The operation is similar when the switching circuitry is under the control of the output comparator 98B. This occurs when switch 19 is operated for heating the output air of the system. Then ground is connected to the emitter of transistor Q4 (which biases it off) through conductor 112 diode CR7 and resistor R66. When this occurs there is no ground on conductor 111 which causes transistor Q3 to conduct and shunt the signal from comparator 98A to ground. Transistor Q2 conducts as long as there is a positive output from amplifier 98B. The emitter of transistor Q2 is tied directly to ground and its collector is tied to the base of transistor Q6 through resistor R61. The emitters of both driver transistors Q5 and Q6 are tied to positive voltage and their collectors are tied to the power transistors. Positive bias is placed on the emitters of transistors Q3 and Q4 through resistors R68 and R69, respectively, tied to the positive voltage bus 113. The junction of the emitters of transistors Q3, Q4 and resistors R68, R69 is coupled to negative voltage through resistors R63, R65, respectively.

The operation of switch 19 to positions 3 or 4 places a ground on one side of the relay coil K2. The other side of the relay coil K2 is connected to negative voltage in parallel with coil K1. A spark suppressing diode CR8 bridges coil K2. A pilot light 16 is connected from negative battery to ground in parallel with the relay coil to indicate availability of the voltage.

When relay K2 is operated, the contact K2A is activated to connect the floating midpoint of the secondary of transformer T2 to the elements 46, 47. Contact K1A is not actuated and remains at ground. The current through elements 46, 47 is in an opposite going direction as compared to the current caused by the operation of relay K1.

Further, it should be noted that contact K1B does not operate in the heat mode because in the heat mode, elements 46, 47 are much more efficient than in the cooling mode and less power is therefore required. In particular, when coil K1 is actuated (cooling mode) contacts K1B connect diode CR9 to one end of transformer T2 enabling transistors Q7, Q8 to provide control of the full wave output from the midpoint of transformer T2. When contacts K2 are activated, contacts K1B are open providing half-wave output from transformer T2, in which case only transistor Q8 is enabled to control this half-wave signal. Thus, in this manner, more power is available in the cooling mode than in the more efficient heating mode.

In the cooling mode transistors Q7 and Q8 operate together under the control of transistors Q5 and Q6 which also operate identically together. Thus, the positive signal received through transistors Q5 and Q6 causes transistors Q7 and Q8 to conduct. The conduction of transistors Q7 and Q8 sends current through elements 46, 47 in a direction to cool outgoing air.

In operation the air can be set for a preset cool or warm temperature or a cool or warm adjustment setting, depending on the position of the wiper of switch 19. The difference between the *set* temperature and the actual temperature causes an output at amplifier 96. The error output of amplifier 96 is used to vary the phase of the output of comparators 98A or 98B. The output of comparator 98A controls the automatic cooling adjustment while the output of amplifier 98B controls the automatic heating adjustment. The phase control and switching circuitry operates responsive to either the output of comparator 98A or comparator 98B to provide a phase controlled signal through elements 46, 47 that is proportional to the error signal. Thus, elements 46, 47 act to heat or to cool for different periods of time, depending on the amplitude of error as determined by element 36. The operator first operates switch 19 for a hot or cold mode desired. Switch 84 is operated to time the injection of air into the ear of the patient. When the desired time has elapsed, a tone generator automatically functions to send an audible signal through a loud speaker. In the meantime, the air of the desired temperature is injected into the ears of the patient.

While the principles of the invention have been described above in connection with specific apparatus and applications, it is to be understood that this description is made only by way of example and not as a limitation on the scope of the invention.

We claim:

1. An air caloric stimulation system for eliciting a nystagmus condition in a patient by stimulating the patient's ear with an air stream of controlled temperature,
   said system comprising air supply means for supplying air under compression,
   nozzle means for applying air from said air supply means to the patient's ear,
   temperature setting means for setting the temperature of the air delivered to the patient's ear to a desired set level,
   sensor means for sensing the actual temperature of the air delivered to the patient's ear,
   power supply means for supplying electrical current,
   thermal element means operating responsive to the duration and direction of the current therethrough for supplying or removing heat from the air,
   means including control circuitry connecting said power supply means to said thermal element means for controlling the current direction and duration through said thermal element means as a function of the difference between said set temperature and said sensed temperature, whereby said thermal element means heats or cools the air until the temperature of the air delivered to the patient's ear equals said set temperature,
   said control circuitry including timing means for indicating the time length of the delivery of the compressed air to the patient's ear.

2. The air caloric stimulation system of claim 1 wherein said control circuit means comprises means for converting said sensed temperature to a first electrical signal,
   means for providing a second electrical signal as an indication of the set temperature, and
   difference means for providing an error signal based on the difference between said first electrical signal and said second electrical signal.

3. The air caloric stimulation system of claim 2 wherein said thermal element comprises at least one Peltier unit, and wherein said temperature setting means includes mode switch means for selectively determining whether the air delivered from the system is to be hot or cold by setting said mode switch means to the heating mode or cooling mode, respectively.

4. The air caloric stimulation system of claim 3 and phase control means operated responsive to the setting of said mode switch means and said error signal for providing current through the Peltier unit.

5. The air caloric stimulation system of claim 4 wherein comparator means are provided for synchronizing said error signal with a line frequency signal,
   said comparator comprising a first comparator amplifier operated responsive to a positive error signal for providing a first control signal with an average duration that is a function of the amplitude of the first error signal, and
   a second comparator amplifier operated responsive to a negative error signal for providing a second control signal with an average duration that is a function of the amplitude of the second error signal.

6. The air caloric stimulation system of claim 4 wherein said first or second control signals control the length of time the current is supplied to the thermal elements,
said first control signal controlling when said mode switch means is in said cooling mode, and
said second control signal controlling when said mode control switch is in said heating mode.

7. An air caloric stimulation system for providing air at controlled temperatures to patient's ears to induce nystagmus,
said system comprising a source of air,
power supply means for supplying electrical current,
thermal element means connected to said power supply means for either heating or cooling the air as a function of electrical current direction through said thermal units,
sensor means for sensing the temperature of the air going into the patient's ears,
means for setting the temperature of the air going into the patient's ear,
switch means for selecting a hot mode or a cold mode of operation to determine whether the air delivered is relatively hot or cold by controlling the direction of the current going through said thermal element means from said power supply means, and
phase control means operating responsive to the difference between said sensed temperature and said set temperature for supplying current to said thermal units for a time period that is a function of the amplitude of said difference.

8. The air caloric stimulation system of claim 7 wherein said thermal units are Peltier units.

9. The air caloric stimulation system of claim 7 wherein liquid exchange equipment is used for cooling said thermal units.

10. The air caloric stimulation system of claim 9 wherein said means for determining the difference between said sensed temperature and the set temperature comprises:
circuit means for converting the sensed temperature to a first signal and for providing a second signal as a function of the set temperature,
means for providing an error signal as a function of the difference between the first signal and said second signal, and
means for using the error signal to control the current duration through said thermal element means.

11. The air caloric stimulation system of claim 9 and means for increasing the power to said Peltier elements in the cold mode of operation.

12. An air caloric stimulation system for eliciting a nystagmus condition in a patient by stimulating the patient's ear with an air stream of controlled temperature,
compressed air supply means,
means for supplying air from said air supply means to the patient's ear,
temperature setting means for setting the temperature of the air delivered to the patient's ear to a desired level,
sensor means for sensing the actual temperature of the air delivered to the patient's ear,
thermal element means for supplying or removing heat from the air supplied to the ear responsive to the duration and direction of current therethrough,
power supply means for supplying electrical current to said thermal element means,
control circuit means for controlling the electrical current from said power supply both as to direction and duration as the electrical current passes through said thermal element means,
said current direction and duration being supplied as a function of the difference between said set temperature and the actual temperature, whereby said actual temperature is made equal to said set temperature by the controlled current passing through the thermal element means,
said control circuit means further including timing means for indicating the time and duration of the delivery of air to the patient's ear, and
said timing means including alarm means to alert an operator of said air caloric stimulation system that a desired amount of time has elapsed.

13. An air caloric stimulation system for providing air at controlled temperatures to a patient's ear to induce nystagmus,
said system comprising: a source of air,
power supply means for supplying electrical current,
Peltier elements connected to said power supply means for heating or cooling the air as a function of electrical current direction through said Peltier elements,
means for setting the temperature of the air going into the patient's ear,
switch means for selecting a hot mode or a cold mode of oepration to determine whether the air delivered is relatively hot or cold,
phase control means operating responsive to the difference between said sensed temperature and said set temperature for supplying current to said Peltier elements for a time period that is a function of the amplitude of said difference,
liquid exchange equipment for cooling said Peltier elements,
said phase control means including means for determining the difference between said set temperature and said sensed temperature and for converting the sensed temperature to a first signal and the set temperature to a second signal,
means for providing an error signal as a function of the difference between the first signal and the second signal,
control means for using the error signal to control the current duration through said Peltier elements, and
said control means including means for synchronizing the error signal to the line frequency to convert the error signal to a square wave signal having a frequency that is twice the line frequency and having the duration of the positive portion varied as a direct function of the amplitude of the error signal.

14. The air caloric stimulation system of claim 13 wherein said synchronizing means comprises a pair of comparators,
a first of said comparators connected directly to the error signal, and
a second of said comparators connected to the error signal through an inverter, whereby the output of the first comparator is used when the error signal is negative and the output of the second comparator is used when the error signal is positive.

15. The air caloric stimulation system of claim 14 wherein said phase control means are operated responsive to the positive signal received from either said first or second comparators and from said switch means used to select the hot or cold mode of operation.

16. The air caloric stimulation system of claim 15 wherein the polarity switching and phase control circuitry includes power transistor means attached to each of said pair of comparators for switching current into opposite sides of said thermal element,
control transistor means operated to turn on for a duration determined by said first comparator means when said error signal is positive and said switch means is in the cooling mode and by said second comparator means when said error signal is negative and said switch means is in the heating mode, and
said switch means connected to select the direction of current through the thermal units by turning it to either the cooling mode or the heating mode.

* * * * *